US007068749B2

(12) United States Patent
Kollegal et al.

(10) Patent No.: US 7,068,749 B2
(45) Date of Patent: Jun. 27, 2006

(54) STATIONARY COMPUTED TOMOGRAPHY SYSTEM WITH COMPACT X RAY SOURCE ASSEMBLY

(75) Inventors: Manohar Gopalaswamy Kollegal, Bangalore (IN); Colin Richard Wilson, Niskayuna, NY (US); Bernard Patrick Bewlay, Schenectady, NY (US); Mark Gilbert Benz, Lincoln, VT (US)

(73) Assignee: General Electric Company, Niskayuna, NY (US)

( * ) Notice: Subject to any disclaimer, the term of this patent is extended or adjusted under 35 U.S.C. 154(b) by 162 days.

(21) Appl. No.: 10/440,695

(22) Filed: May 19, 2003

(65) Prior Publication Data

US 2004/0234023 A1 Nov. 25, 2004

(51) Int. Cl.
*A61B 6/00* (2006.01)
*G01N 23/083* (2006.01)
*G21K 1/10* (2006.01)
*H01J 35/00* (2006.01)

(52) U.S. Cl. .......................... 378/10; 378/9; 378/138; 378/141

(58) Field of Classification Search .................. 378/9, 378/10, 138, 141, 123
See application file for complete search history.

(56) References Cited

U.S. PATENT DOCUMENTS

| 4,145,616 | A | * | 3/1979 | Tanabe | 378/150 |
| 5,128,977 | A | * | 7/1992 | Danos | 378/121 |
| 5,268,955 | A | * | 12/1993 | Burke et al. | 378/135 |
| 5,491,734 | A |   | 2/1996 | Boyd et al. | 378/10 |
| 5,654,995 | A |   | 8/1997 | Flohr | 378/10 |
| 5,745,546 | A | * | 4/1998 | Hell et al. | 378/143 |
| 5,764,722 | A |   | 6/1998 | Voss | 378/10 |
| 6,005,918 | A | * | 12/1999 | Harris et al. | 378/140 |
| 6,301,332 | B1 | * | 10/2001 | Rogers et al. | 378/142 |
| 6,385,292 | B1 | * | 5/2002 | Dunham et al. | 378/122 |
| 6,619,841 | B1 | * | 9/2003 | Lenz | 378/200 |
| 6,807,248 | B1 | * | 10/2004 | Mihara et al. | 378/10 |
| 2004/0202282 | A1 | * | 10/2004 | Miller | 378/140 |

FOREIGN PATENT DOCUMENTS

GB 2120060 A * 11/1983

OTHER PUBLICATIONS

Dutch Search Report, Mar. 17, 2005.

* cited by examiner

*Primary Examiner*—Edward J. Glick
*Assistant Examiner*—Krystyna Suchecki
(74) *Attorney, Agent, or Firm*—Jean K. Testa; Donald S. Ingraham

(57) ABSTRACT

A stationary CT system comprising at least one annular x ray source assembly comprising a plurality of respective x ray sources spaced along the annular x ray source assembly. Each of the x ray sources comprises a respective stationary x ray target, an electron beam focusing chamber; an x ray channel; an electron beam source disposed in a spaced apart relationship with respect to the respective stationary x ray target; a vacuum chamber disposed in between the electron beam focusing chamber and an insulating chamber where the insulating chamber houses the electron beam source; a radiation window at a pre-defined angular displacement from the respective stationary x ray target and the x ray channel; and a target substrate attached to the respective stationary x ray target.

61 Claims, 10 Drawing Sheets

STATIONARY COMPUTED TOMOGRAPHY SYSTEM WITH COMPACT X RAY SOURCE ASSEMBLY

BACKGROUND OF THE INVENTION

The present invention relates generally to a Computed Tomography (CT) system and specifically to a stationary CT system with a compact x ray source assembly.

Computed tomography (CT) is a technique which creates two-dimensional cross-sectional images from three-dimensional body structures. The CT imaging system primarily includes a CT gantry and a patient table or a couch. The gantry is a moveable frame that contains a x-ray source which is typically a x ray tube including collimators and filters, detectors, data acquisition system (DAS), rotational components including slip ring systems and all associated electronics such as gantry angulation motors and positioning laser lights.

In known third generation CT systems (spiral/helical), the x ray source and the detector array are rotated with a gantry within the imaging plane and around the object to be imaged so that the angle at which the x ray beam intersects the object constantly changes. X ray sources typically include x ray tubes, which emit the x ray beam at a focal spot. An x ray detector is a crystal or ionizing gas that when struck by an x-ray photon produces light or electrical energy. The two types of detectors utilized in CT systems are scintillation or solid state and xenon gas detectors. The CT systems may typically include post patient collimators for reducing scattered radiation at the detector.

Current third generation CT systems involve rotating an x ray source around the patient to do body scans and have limitations regarding scanning speeds.

Next generation CT architectures, which include stationary CT concept, offer high scan speeds and they involve directing high power, fast moving electron beams onto stationary x ray targets to produce x rays. The Stationary CT concept presents unique challenges in the target and geometric design of the compact x ray producing apparatus in CT scan systems. There are significant thermal and structural risks associated with the impact of focused, high power electron beam on the stationary x ray target and the resulting heat distribution on the various components of the stationary CT systems.

It is therefore desirable to provide compact CT system geometries that mitigate the thermal and structural risks and can house the principal CT system components including the stationary target, electron beam source, focusing chamber and radiation window, and also meet high power and faster scans requirements of advanced CT systems.

BRIEF DESCRIPTION OF THE INVENTION

Briefly, in accordance with one embodiment of the present invention, a stationary CT system comprises at least one annular x ray source assembly comprising a plurality of respective x ray sources spaced along the annular x ray source assembly. Each of the respective x ray sources comprises a respective stationary x ray target, an electron beam focusing chamber, an x ray channel, and an electron beam source disposed in a spaced apart relationship with respect to the respective stationary x ray target. The electron beam focusing chamber has a selected cross-sectional profile so as to focus a plurality of electrons emitted from the electron beam source to impinge on the respective stationary x ray target to produce x rays that pass into the x ray channel.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present invention describes suitable stationary CT embodiments which combine the primary source components including a stationary x ray target 102, an electron beam source 108, an electron beam focusing chamber 104 and high heat flux cooling into a compact form and thereby enable stationary CT introduction.

Figure 1:
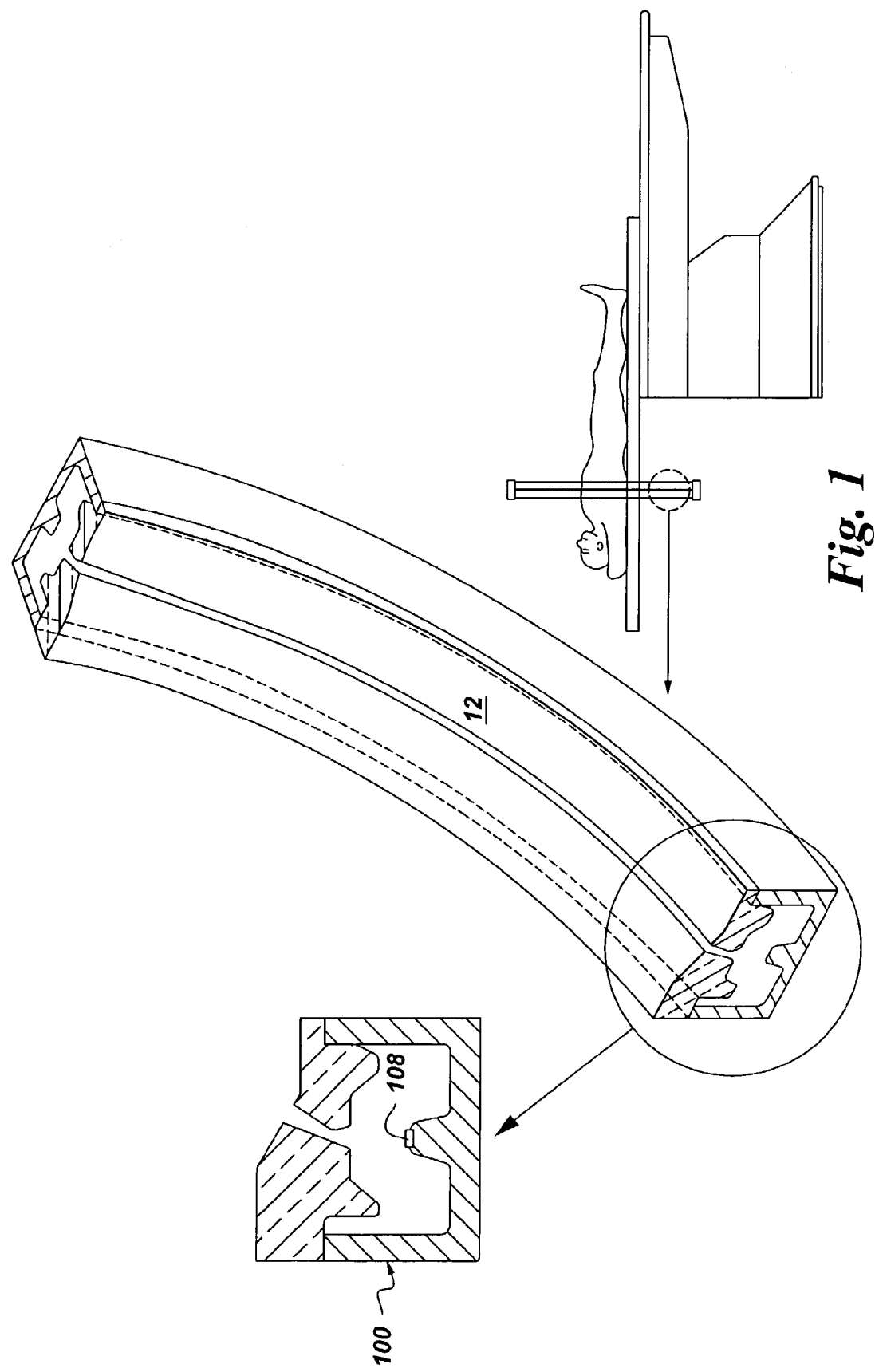
FIG. 1 illustrates a sectional view of a stationary CT system comprising an annular x ray source assembly.
Figure 2:
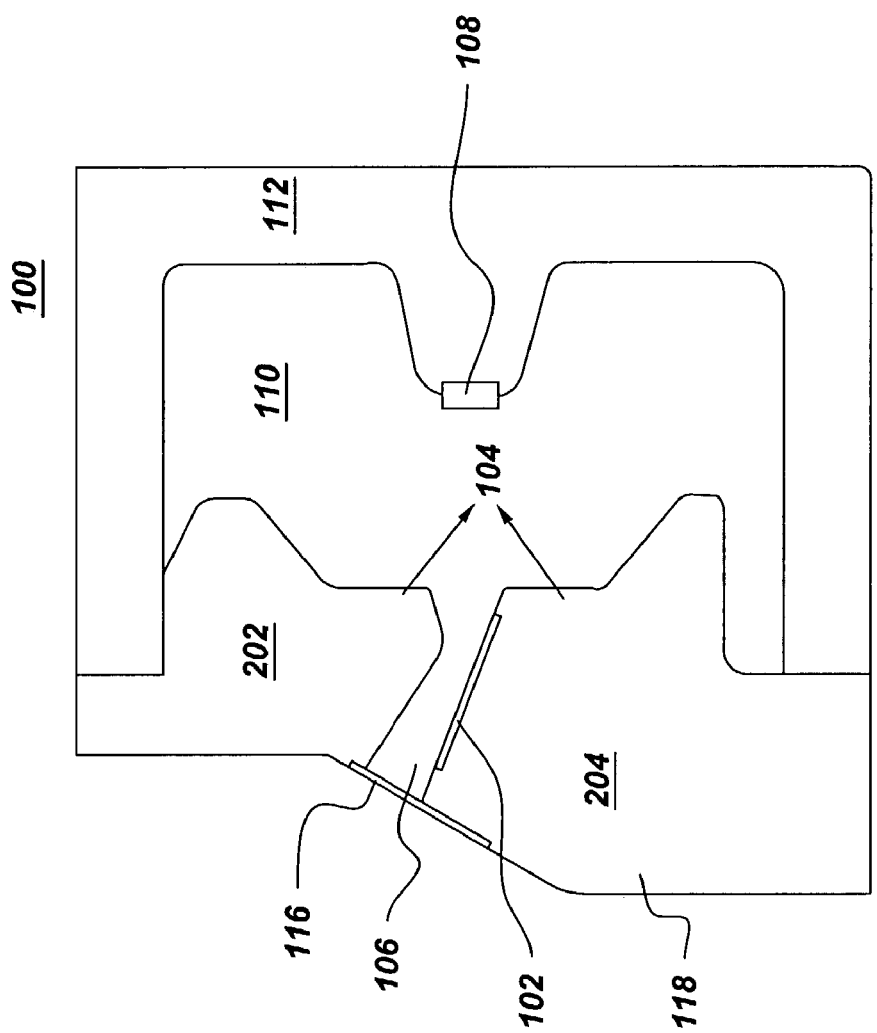
FIG. 2 illustrates a cross-sectional view of a x ray source in an annular x ray source assembly.

FIG. 1, illustrates a sectional view of stationary CT system 10 which, in one embodiment, comprises at least one annular x ray source assembly 12 comprising a plurality of respective x ray sources 100 spaced along the annular x ray source assembly 12. In one specific embodiment as illustrated in FIG. 2, each of the x ray sources 100 comprises a respective stationary x ray target 102, an electron beam focusing chamber 104, an x ray channel 106, and an electron beam source 108 disposed in a spaced apart relationship with respect to the respective stationary x ray target 102. The spaced apart relationship is such that the electron beam emanating from the electron beam source 108 is incident on x-ray target 102 at a low angle of around twenty degrees. The electron beam focusing chamber 104 comprises a portion of vacuum chamber 110; the beam focusing chamber 104 has a selected cross-sectional profile (that is, the arrangement of chamber 104 as defined by a top section 202, a bottom section 204, including the shape of the interior walls defined by such sections, the spacing between walls, and the spaced relationship with components, such as beam source 108 and x-ray channel 106) so as to focus a plurality of electrons emitted from the electron beam source 108 to impinge on the respective stationary x ray target 102 to produce x rays that pass into the x ray channel 106. The selected cross-sectional profile is based on electron optics considerations to ensure correct beam focusing to the point of target impact.

Vacuum chamber 110 is disposed in between the electron beam focusing chamber 104 and an insulating chamber 112 as illustrated in FIG. 2. FIG. 2 also illustrates that the x ray channel 106 is an extension of the vacuum chamber 110.

The electron beam source 108, is electrically isolated from the respective stationary x ray target 102 by housing it in the insulator chamber 114 (FIG. 5) comprising an insulator medium such as a high temperature ceramic or a plastic, for example ULTEM® manufactured by GE Plastics. In one example, the electron beam source 108 housed in the insulating chamber 112 is adapted to be maintained at a negative potential with respect to the vacuum chamber 110 and electron beam focusing chamber 104 and the stationary x ray target 102 is grounded. As used herein, "adpated to" and the like refers to an electrical arrangement of conductors, insulators, and electrical sources by which an electrical potential may be maintained between components). In another example, the electron beam source 108 is grounded and the stationary x ray traget 102 is maintained at a positive potential. Alternately, in another example, the electron beam source 108 is maintained at a negative potential while the stationary x ray target 102 is maintained at a positive potential.

The electron beam source 108 comprises a filament or a field emitter array. The filament typically comprises a coiled filament or a flat filament, examples of which are known in the art.

Figure 3:
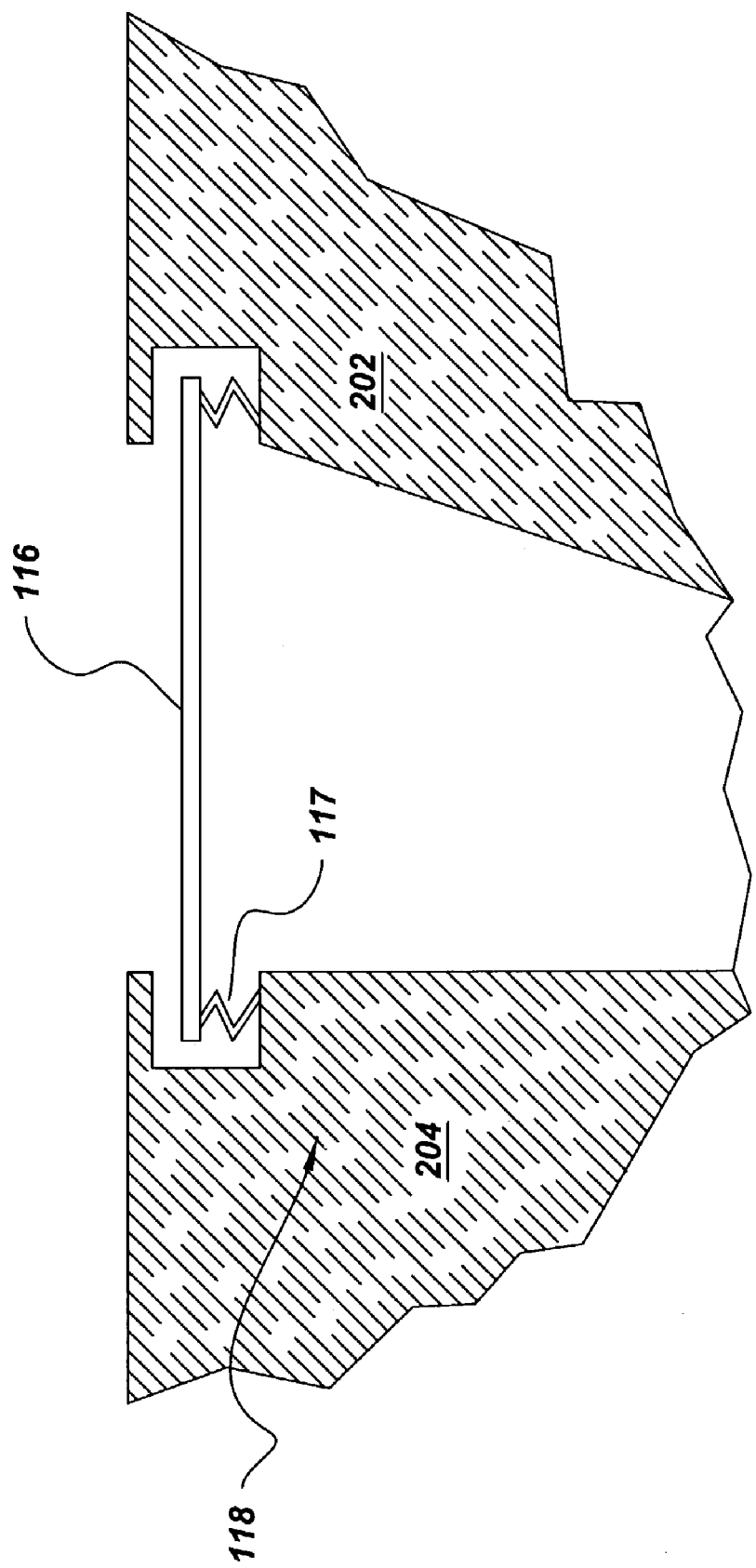
FIG. 3 illustrates radiation window with compliant devices to reduce thermal stresses in one embodiment of the invention.

In one specific embodiment, each of the x ray sources 100 of FIG. 2 further comprises a radiation window 116 at a pre-defined angular displacement from the respective stationary x ray target 102 and the x ray channel 106. The radiation window 116 is used as an exit path for a plurality of x rays produced by the respective stationary x ray target 102. The pre-defined angular displacement ensures maximum x ray flux exit from the radiation window 116. The radiation window 116 comprises a material such as aluminum or beryllium. In order to relieve thermal stresses that are likely to develop at the window attachment areas due to thermal cycling, suitable compliant devices 117 similar to the one indicated in FIG. 3 are used in one embodiment of the invention. The compliant devices 117 could be springs or any conventional flexible material. In another specific embodiment, the radiation window 116 is coupled to the target substrate 118 and the selected cross-sectional profile of the electron beam focusing chamber 104 by a brazed contact. In an alternate embodiment this coupling is achieved by means of a mechanical contact. In one embodiment, the radiation window 116 and the supporting cross-section of the electron beam focusing chamber 104 are electrically isolated from the respective stationary x ray target 102 by means of a small gap 201 in the gap (FIG. 5) between outer surface of x ray source 100 and x ray target 102. In another embodiment, the radiation window 116 is at a negative bias with respect to the respective stationary x ray target 102 which helps to reduce the amount of electron deposition at the radiation window 116 and this further leads to lower peak temperatures and stresses on the radiation window 116.

The stationary x ray target 102 as described in above embodiments comprises metal or metal alloys having an atomic number of at least about 40. The metal and metal alloys are selected from a group of Tungsten, Molybdenum, Rhenium, Rhodium and Zirconium.

In another embodiment, each of the x ray sources 100 further comprises a target substrate 118 (FIG. 2) attached to the respective stationary x ray target 102. The target substrate 118 is also shaped to form a bottom part of selected cross-sectional profile of the electron beam focusing chamber 104 as illustrated in FIG. 2. The target substrate 118 comprises a high thermal conductivity material having a thermal conductivity greater than about 75 W/m/K. Such high thermal conductivity materials are selected from a group of copper, aluminum, graphite, graphite foams and metal foams of aluminum and copper. The stationary x ray target 102 and the high thermal conductivity target substrate 118 are grounded and are maintained at zero potential or alternately the stationary x ray target 102 and the target substrate 118 are at positive bias with respect to the electron beam source 108 and radiation window 116.

Figure 4:
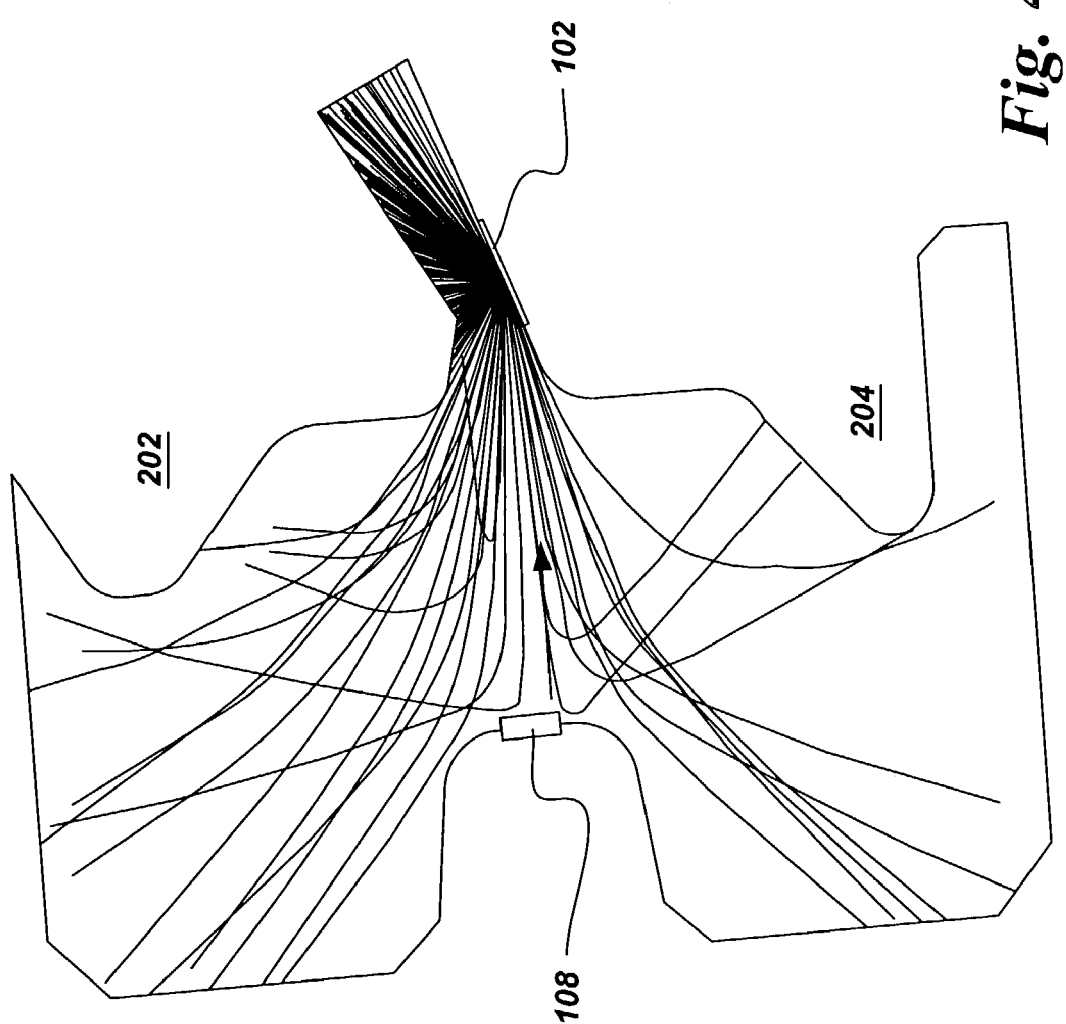
FIG. 4 illustrates an electron beam scatter profile in a vaccum chamber and x ray channel of FIG. 2.

In a more specific embodiment, the selected cross-sectional profile of the electron beam focusing chamber 104 comprises a contoured enclosure comprising a top section 202 and a bottom section 204 separated by the x ray channel 106 as illustrated in FIG. 2. The top section 202 and the bottom section 204 comprise a high thermal conductivity material such as copper, aluminum, graphite, graphite foams or metal foams of aluminum and copper in one embodiment of the invention. The top section 202 receives much of the back-scatter electrons as a result of impact of the electron beam on the respective stationary x ray target 102, which is illustrated in FIG. 4.

Figure 5:
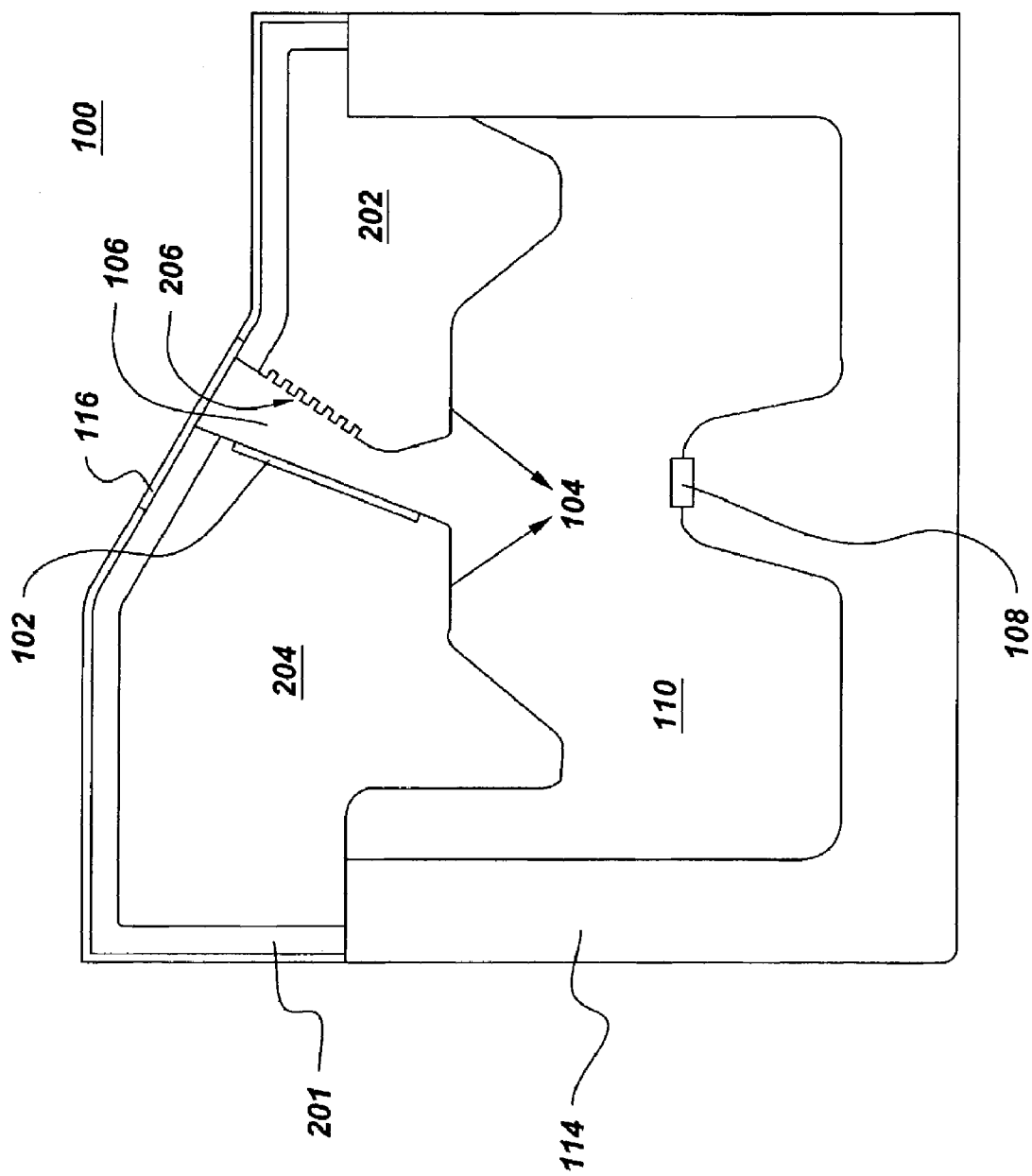
FIG. 5 illustrates an embodiment with grooves to prevent back-scattered electrons from striking a stationary x ray target.

To address the issue of the back-scattered electrons, in one specific embodiment, the portion of section 202 disposed adjacent to channel 106 comprises a plurality of grooves 206 cut into it as illustrated in FIG. 5. These grooves 206 are located in a region opposite the respective stationary x ray target 102 and disposed to trap the plurality of back-scattered electrons and to prevent these back-scattered electrons from hitting the respective stationary x ray target 102. In one specific example such grooves 206 measure about 3–4 mm deep and 2 mm wide. These grooves 206 also increase the surface area of heating and facilitate cooling in this region.

Figure 6:
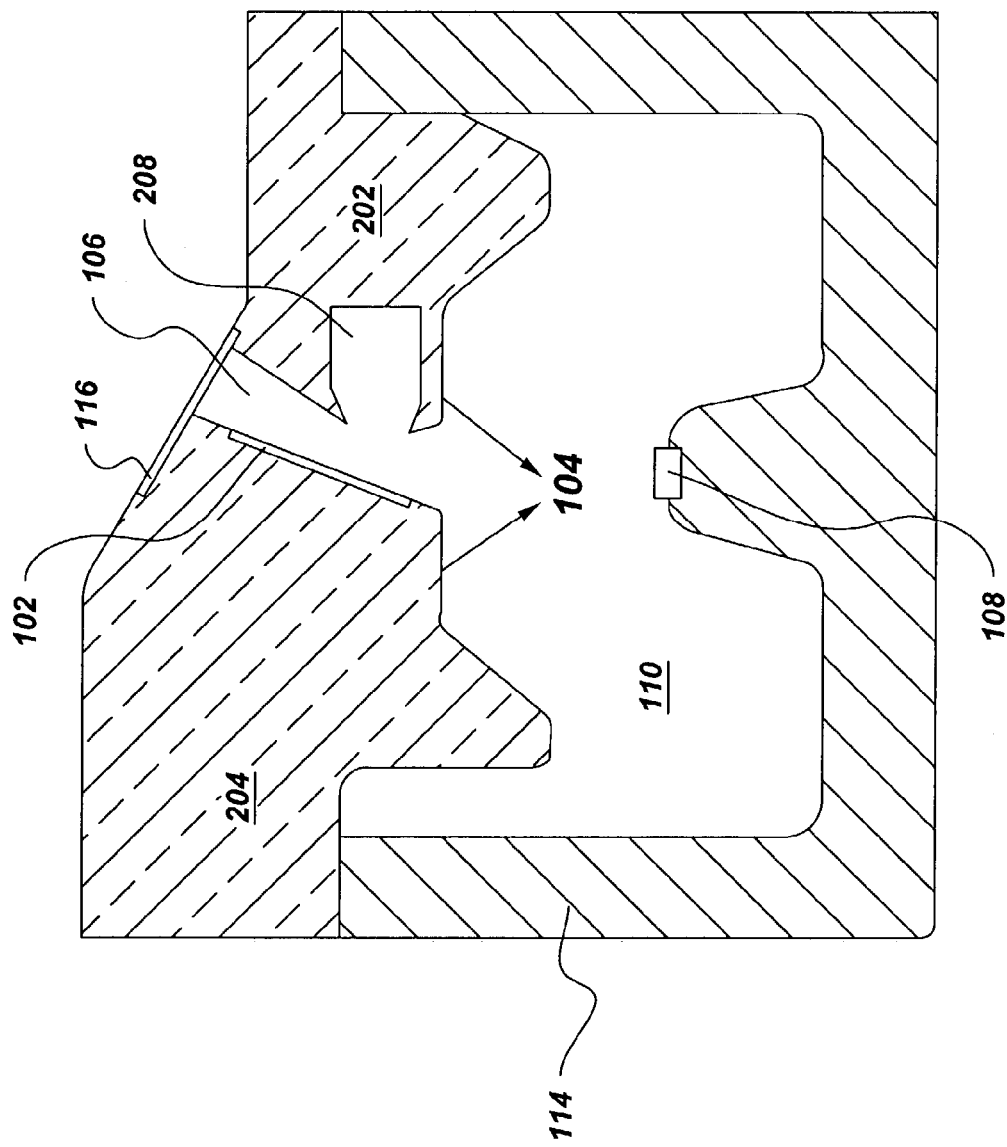
FIG. 6 illustrates an embodiment with a notch to prevent back-scattered electrons from striking a stationary x ray target.

In an alternative embodiment as shown in FIG. 6, the portion of section 202 disposed adjacent to channel 106 comprises a notch 208 located opposite the respective stationary x ray target 102 to trap the plurality of back-scattered electrons and to prevent these back-scattered electrons from hitting the respective stationary x ray target 102. In one specific example such a notch 208 measures about 9.1 mm wide and 12 mm deep.

Figure 7:
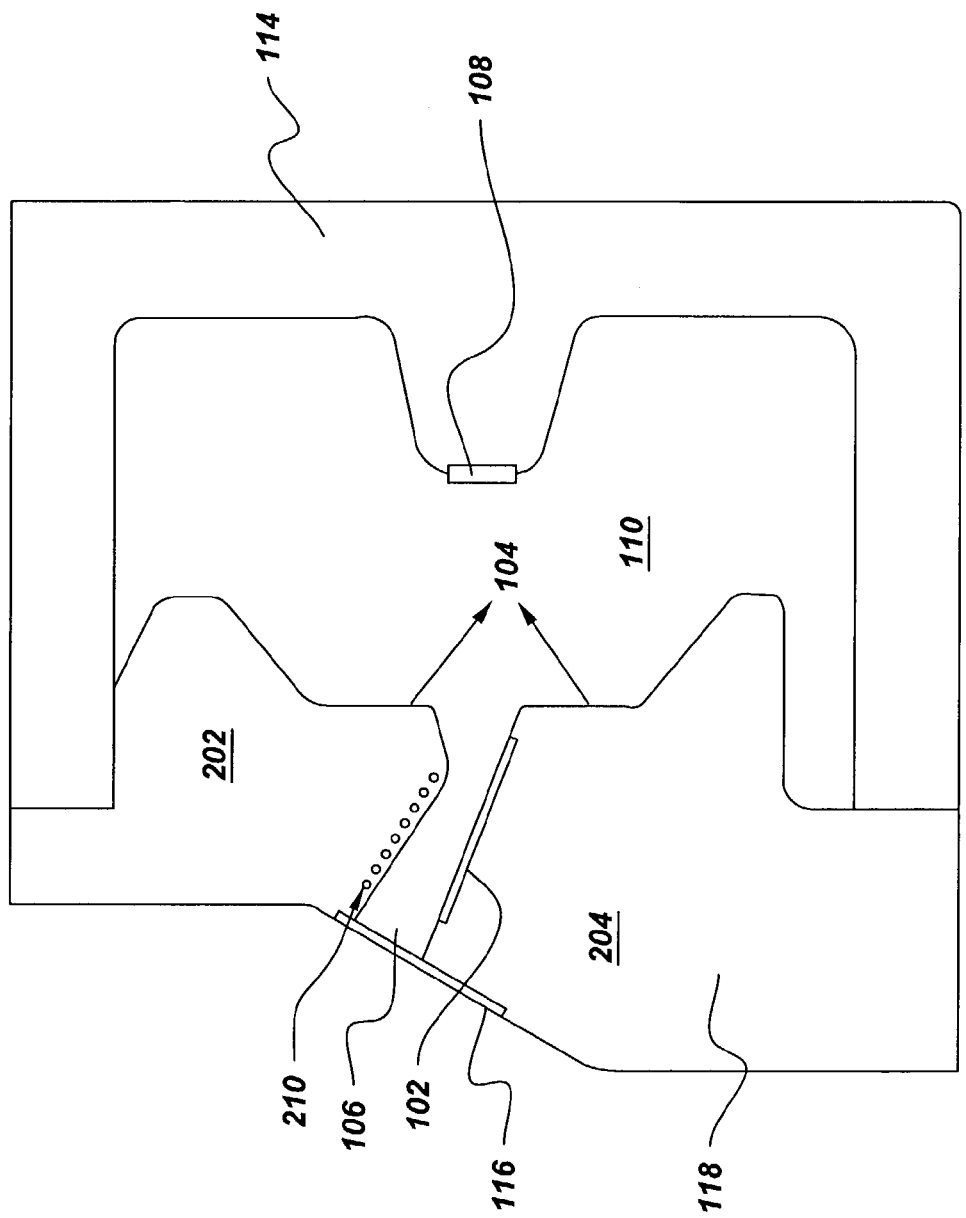
FIG. 7 illustrates an embodiment having a plurality of cooling channels in the top section of the electron beam focusing chamber of FIG. 2.

In yet another embodiment as shown in FIG. 7, the top section 202 of the selected cross-sectional profile of the electron beam focusing chamber 104 comprises a plurality of cooling channels 210 for cooling the region opposite the respective stationary x ray target 102 which gets heated due to the impact of the back-scattered electrons in this region. A coolant is passed through the cooling channels 210 to dissipate this heat. The coolant comprises at least one of water or a liquid which acts as a suitable coolant such as FLUORINERT™ manufactured by 3M™. In an alternate embodiment, the cooling channels 210 comprise heat storage materials to dissipate the heat. These heat storage materials, in one specific embodiment comprise phase change materials such as paraffin. In another embodiment the heat storage materials comprise at least one of sodium, potassium, tin, lead, indium, antimony, bismuth, sodium-potassium alloy, tin-lead alloy and indium-antimony alloy.

Figure 8:
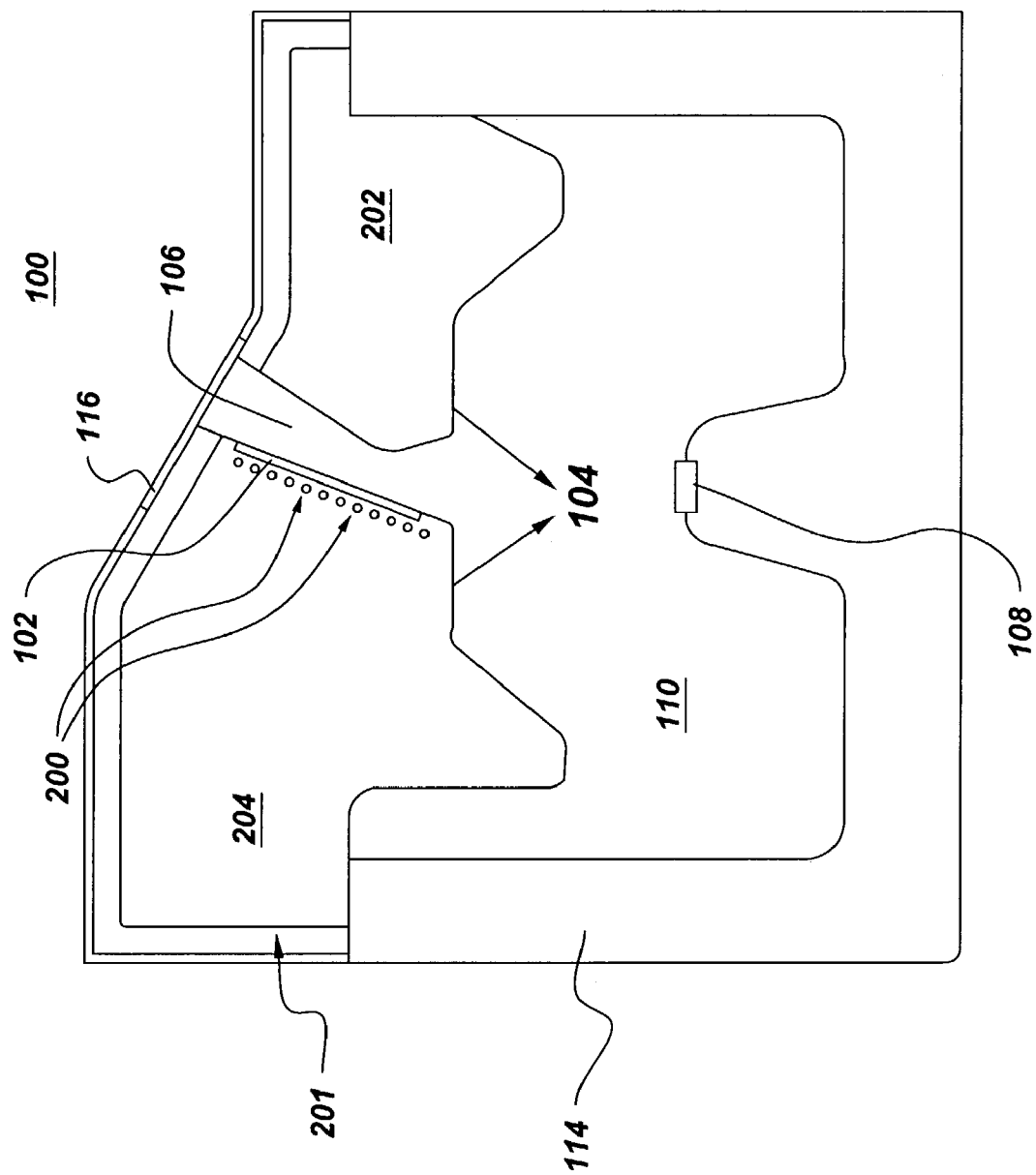
FIG. 8 illustrates an embodiment with a plurality of cooling channels in the target substrate of FIG. 2.

Due to the continous impact of electrons on the stationary x ray target 102, it is deisrable to provide cooling mechanisms to protect the stationary x ray target 102 from the thermal stresses in the region. In one specific embodiment, the target substrate 118 comprises a plurality of cooling channels 200 just below the respective stationary x ray target 102 region as shown in FIG. 8. In one embodiment these are small circular cross-section channels, which in one specific example are of about 3–4 mm diameter and spaced 4 mm apart, drilled within the target substrate 118, beneath the respective stationary x ray target 102. Coolant such as water or a liquid which acts as a suitable coolant such as FLUORINERT™ manufactured by 3M™, is pumped through the channels for facilitating faster heat removal from the respective stationary x ray target 102. Alternately, the cooling channels 200 comprise heat storage materials to dissipate heat generated at the respective stationary x ray target 102. The heat storage materials in one example comprise phase change materials. These phase change materials include paraffin. In another embodiment the heat storage materials comprise at least one of sodium, potassium, tin, lead, indium, antimony, bismuth, sodium-potassium alloy, tin-lead alloy and indium-antimony alloy.

Figure 9:
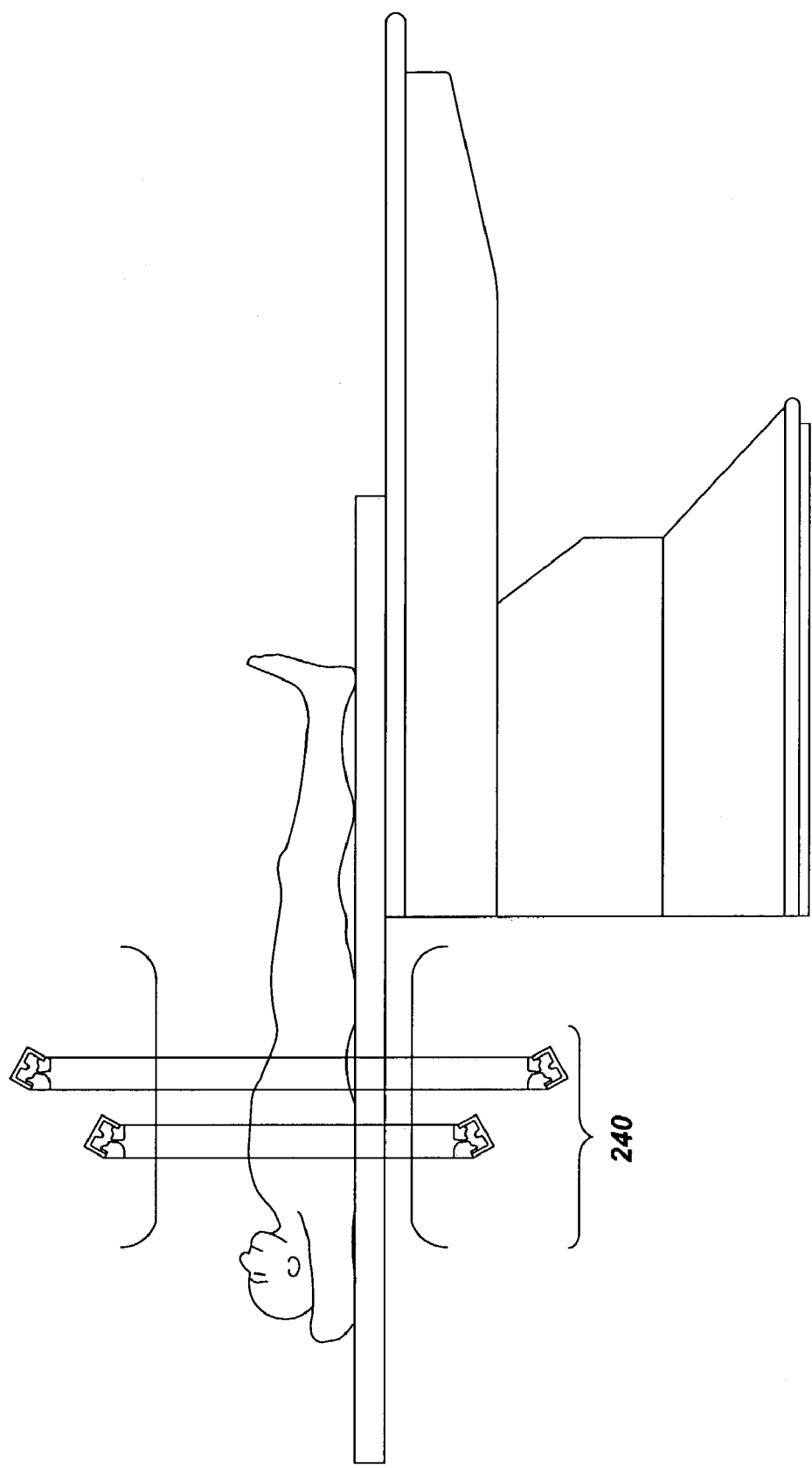
FIG. 9 illustrates an embodiment of a stationary CT system comprising a plurality of annular x ray source assemblies.

Yet another embodiment is a stationary CT system 10 as illustrated in FIG. 9, which comprises a plurality of x ray source assemblies 240, where each of the plurality of x ray source assemblies 240 comprises a plurality of respective x ray sources 100 spaced along each of respective annular x ray assemblies. The plurality of x ray source assemblies 240 can be of varying annular diameters. Each of the plurality of respective x ray sources 100 comprises a respective stationary x ray target 102, an electron beam focusing chamber 104, an x ray channel 106, and an electron beam source 108. The electron beam source 108 is disposed in a spaced apart relationship with respect to the respective stationary x ray target 102. The electron beam focusing chamber 104 has a selected cross-sectional profile so as to focus a plurality of electrons emitted from the electron beam source 108 in order to impinge on the respective stationary x ray target 102 to produce x rays that pass into the x ray channel 106.

The various embodiments and examples described with respect to the x ray source 100 of FIG. 1 are also applicable to the stationary CT system 10 of FIG. 9.

Figure 10:
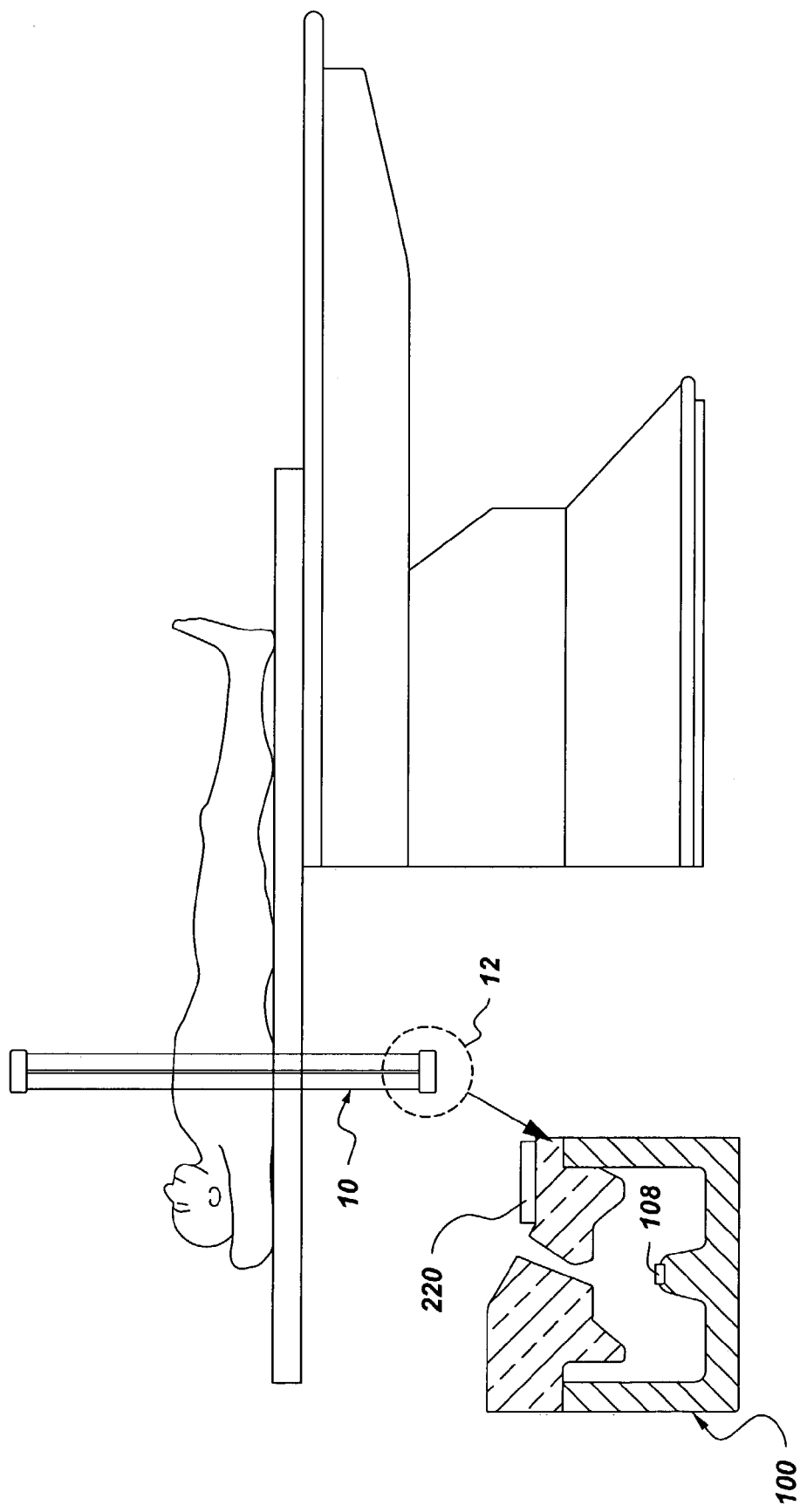
FIG. 10 illustrates an embodiment comprising detectors located along the annular length of the x ray source assembly and spaced at an offset away from the annular x-ray source assembly.

In the above embodiments, the detectors 220 are located along the annular length of the annular x ray source assembly 12 and are spaced at an offset away from the annular x-ray source assembly 12 to ensure optimal x-ray photon flux detection as illustrated in FIG. 10. 'Offset away' means that the the detectors 220 are disposed so that x-rays emanating from the adjacent annular x ray source assembly 12 are not incident on the adjacent detector.

The various features described in the embodiments hereinabove are not necessarily exclusive to each other. Several combinations of the above features are possible for example an embodiment with cooling channels 200 in the target substrate 118 and a notch 208 in the top section 202 of the electron beam chamber 104. Similarly another embodiment comprises cooling channels 200 in the target substrate 118 and grooves 206 in the top section 202 of the electron beam focusing chamber 104. These embodiments can have an additional feature of cooling channels 210 in the top section 202 of the electron beam focusing chamber 104.

Referring to FIG. 10, a sectional profile of a stationary CT system 10 comprises an annular x ray source assembly 12. The annular x ray source assembly comprises x ray sources 100 comprising features described in the various embodiments discussed hereinabove. The x ray sources 100 project a beam of x-rays toward a detector 220 opposite the position of the source on the annular assembly. The detector 220 is typically formed by a plurality of detection elements which together sense the projected x-rays that pass through a patient. Each detection element produces an electrical signal that represents the intensity of an impinging x-ray beam and hence, the attenuation of the beam as it passes through the patient.

The operation of the x-ray source 100 is governed by a control mechanism (not shown) of the stationary CT system 10. The control mechanism includes an x-ray controller that provides power and timing signals to the x-ray source. A data acquisition system (DAS) in the control mechanism samples analog data from the detection elements and converts the data to digital signals for subsequent processing. An image reconstructor receives sampled and digitized x-ray data from the DAS and performs high speed image reconstruction. The reconstructed image is applied as an input to a computer which stores the image in a mass storage device.

The computer (not shown) also receives and supplies signals via a user interface or graphical user interface (GUI). Specifically, the computer receives commands and scanning parameters from an operator console that preferably includes a keyboard and mouse (not shown). An associated cathode ray tube display allows the operator to observe the reconstructed image and other data from the computer. The operator supplied commands and parameters are used by the computer to provide control signals and information to the x-ray controller, the DAS, and a table motor controller in communication with a table to control operation of and movement of the stationary CT system 10 components.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A stationary CT system comprising:
   at least one annular x ray source assembly comprising a plurality of respective x ray sources spaced along said annular x ray source assembly,
   wherein each of said respective x ray sources comprises a respective stationary x ray target; an electron beam focusing chamber; an x ray channel; and an electron beam source disposed in a spaced apart relationship with respect to said respective stationary x ray target, and wherein said electron beam focusing chamber comprises a top section and a bottom section disposed in a spaced relationship to one another so as to have a selected cross-sectional profile so as to focus a plurality of electrons emitted from said electron beam source to impinge on said respective stationary x ray target to produce x rays that pass into said x ray channel, the top section further being configured to receive back-scattered electrons generated by the electron beam impact at the respective stationary x ray target and predominantly redirect the back-scattered electrons away from said electron beam source,
   wherein said top section of said electron beam focusing chamber comprises a plurality of grooves located opposite said respective stationary x ray target to trap a plurality of back-scattered electrons and prevent said plurality of back-scattered electrons from hitting said respective stationary x ray target.

2. The system of claim 1, further comprising a plurality of detectors located along the annular length and spaced at an offset away from the annular x-ray source assembly to ensure optimal x-ray photon flux detection.

3. The system of claim 1, wherein each of said x ray sources further comprises a vacuum chamber disposed in between said electron beam focusing chamber and an insulating chamber, wherein said insulating chamber houses said electron beam source.

4. The system of claim 3, wherein said insulator chamber comprises an insulator medium.

5. The system of claim 4, wherein said insulator medium comprises at least one of a high temperature ceramic and a plastic.

6. The system of claim 3, wherein said electron beam source is adapted to be maintained at a negative potential with respect to said vacuum chamber and said electron beam focusing chamber.

7. The system of claim 1, wherein each of said x ray sources further comprises a radiation window at a predefined angular displacement from said respective stationary x ray target and said x ray channel.

8. The system of claim 7, wherein said radiation window is used as an exit path for a plurality of x rays produced by said respective stationary x ray target.

9. The system of claim 7, wherein radiation window comprises a material, wherein said material comprises at least one of aluminum and beryllium.

10. The system of claim 7, wherein said radiation window and said electron beam focusing chamber are coupled by a brazed contact.

11. The system of claim 7, wherein said radiation window and said electron beam focusing chamber are coupled by a mechanical contact.

12. The system of claim 7, wherein said radiation window is electrically isolated from said respective stationary x ray target.

13. The system of claim 12, wherein said radiation window is at a negative bias with respect to said respective stationary x ray target.

14. The system of claim 1, wherein said respective stationary x ray target comprises at least one of a metal and a metal alloy having an atomic number of at least about 40.

15. The system of claim 14, wherein said metal and said metal alloy comprise at least one selected from a group of Tungsten, Molybdenum, Rhenium, Rhodium and Zirconium.

16. The system of claim 1, wherein each of said x ray sources further comprises a target substrate attached to said respective stationary x ray target.

17. The system of claim 16, wherein said target substrate forms a bottom section of said electron beam focusing chamber and wherein said target substrate comprises a high thermal conductivity material selected from a group of copper, aluminum, graphite, graphite foams and metal foams of aluminum and copper.

18. The system of claim 16, wherein said target substrate comprises high thermal conductivity material having thermal conductivity greater than about 75 W/m/K.

19. The system of claim 16, wherein said respective stationary x ray target and said target substrate are at zero potential, and wherein said electron beam source is at negative potential.

20. The system of claim 16, wherein said respective stationary x ray target and said target substrate are at positive bias and said electron beam source is at negative bias.

21. The system of claim 18. wherein said respective stationary x ray target and said target substrate are at positive bias and said electron beam source is grounded.

22. The system of claim 16, wherein said target substrate comprises a plurality of cooling channels.

23. The system of claim 22, wherein said cooling channels are disposed such that a coolant can pass therethrough so to dissipate heat generated at said respective stationary x ray target.

24. The system of claim 22, wherein said cooling channels comprise heat storage materials to dissipate heat generated at said respective stationary x ray target.

25. The system of claim 24, wherein said heat storage materials comprise phase change materials, and wherein said phase change material comprise paraffin.

26. The system of claim 24, wherein said heat storage materials comprise at least one of sodium, potassium, tin, lead, indium, antimony, bismuth, sodium-potassium alloy, tin-lead alloy and indium-antimony alloy.

27. The system of claim 1, wherein said top section end said bottom section comprise a high thermal conductivity material selected from a group of copper, aluminum, graphite, graphite foams and metal foams of aluminum and copper, said top section and said bottom section defining a portion of an interior wall of said electro beam focusing chamber, the shape of said wall defining a portion of said selected cross sectional profile.

28. The system of claim 27, wherein said top section of said electron beam focusing chamber comprises a notch located opposite said respective stationary x ray target to trap a plurality of back-scattered electrons and to prevent said plurality of back-scattered electrons from hitting said respective stationary x ray target.

29. The system of claim 27, wherein said top section of said electron beam focusing chamber comprises a plurality of cooling channels.

30. The system of claim 29, wherein said cooling channels are configured to allow a coolant to be passed through said cooling channels and wherein said coolant comprises a liquid.

31. The system of claim 29, wherein said cooling channels comprise heat storage materials.

32. The system of claim 31, wherein said heat storage materials comprise phase change materials, wherein said phase change material comprise paraffin.

33. The system of claim 31, wherein said heat storage materials comprise at least one of sodium, potassium, tin, lead, indium, bismuth, sodium-potassium alloy, tin-lead alloy and indium-antimony alloy.

34. The system of claim 1, wherein the structure surrounding said electron beam focusing chamber comprises of high thermal conductivity material and wherein said high thermal conductivity material comprises at least one of copper, aluminum, graphite foams and metal foams of aluminum and copper.

35. The system of claim 1, wherein said electron beam source comprises a filament, wherein said filament is at least one of coiled filament and flat filament.

36. The system of claim 1, wherein said electron beam source comprises a field emitter array.

37. A stationary CT system comprising:
a plurality of x ray source assemblies, wherein each of said plurality of x ray source assemblies comprises a plurality of respective x ray sources spaced along each of respective annular x ray source assemblies,
wherein each of said plurality of respective x ray sources comprises, a respective stationary x ray target; an electron beam focusing chamber; an x ray channel; and an electron beam source disposed in a spaced apart relationship with respect to said respective stationary x ray target, and wherein said electron beam focusing chamber comprises a top section and a bottom section disposed in a spaced relationship to one another so as to have a selected cross-sectional profile so as to focus a plurality of electrons emitted from said electron beam source to impinge on said respective stationary x ray target to produce x rays that pass into said x ray channel, the top section further being configured to receive back-scattered electrons generated by the electron beam impact at the respective stationary x ray target and predominantly redirect the back-scattered electrons away from said electron beam source, wherein said too section comprises a plurality of grooves to trap a plurality of back-scattered electrons and prevent said plurality of back-scattered electrons from hitting said respective stationary x ray target.

38. The system of claim 37, wherein each of said plurality of respective x ray sources further comprises a vacuum chamber disposed in between said electron beam focusing chamber and an insulating chamber, wherein said insulating chamber houses said electron beam source.

39. The system of claim 37, wherein each of said plurality of respective x ray sources further comprises a radiation window at a pre-defined angular displacement from said respective stationary x ray target and said x ray channel, and wherein said radiation window is used as an exit path for a plurality of x rays produced by said respective stationary x ray target.

40. The system of claim 39, wherein said radiation window and said electron beam focusing chamber are coupled by a brazed contact.

41. The system of claim 39, wherein said radiation window and said electron beam focusing chamber are coupled by a mechanical contact.

42. The system of claim 37, wherein each of said plurality of respective x ray sources further comprises a target substrate attached to said respective stationary x ray target.

43. The system of claim 42, wherein said target substrate forms a bottom section of said electron beam focusing chamber.

44. The system of claim 42, wherein said target substrate comprises a plurality of cooling channels.

45. The system of claim 44, wherein a coolant is passed through said cooling channels to dissipate heat generated at said respective stationary x ray target and wherein said coolant comprises a liquid.

46. The system of claim 44, wherein said cooling channels comprise heat storage materials to dissipate heat generated at said respective stationary x ray target.

47. The system of claim 37, wherein said top section and said bottom section defining a portion of an interior wall of said electron beam focusing chamber, the shape of said wall defining a portion of said selected cross sectional profile.

48. The system of claim 47, wherein said top section said comprises a notch to trap a plurality of back-scattered electrons and to prevent said plurality of back-scattered electrons from hitting said respective stationary x ray target.

49. The system of claim 47, wherein said top section comprises a plurality of cooling channels.

50. The system of claim 49, wherein said cooling channels are configured to allow a coolant to be passed through said cooling channels and wherein said coolant comprises a liquid.

51. The system of claim 49, wherein said cooling channels comprise heat storage materials.

52. The system of claim 51, wherein said heat storage materials comprise phase change materials.

53. A stationary CT system comprising;
at least one annular x ray source assembly comprising a plurality of respective x ray sources spaced along said annular x ray source assembly, wherein each of said x ray sources comprises,
at respective stationary x ray target; an electron beam focusing chamber; an x ray channel;
an electron beam source disposed in a spaced apart relationship with respect to said respective stationary x ray target, and wherein said electron beam focusing chamber has a selected cross-sectional profile so as to focus a plurality of electrons emitted from said electron beam source to impinge on said respective stationary x ray target to produce x rays that pass into said x ray channel;
a vacuum chamber disposed in between said electron beam focusing chamber and an insulating chamber, wherein said insulating chamber houses said electron beam source;
a radiation window at a pre-defined angular displacement from said respective stationary x ray target and said x ray channel; and
a target substrate attached to said respective stationary x ray target, wherein said target substrate forms a bottom section of said electron beam focusing chamber,
wherein said selected cross-sectional profile of said electron beam focusing chamber comprises a top section and a bottom section disposed in a spaced relationship to one another, wherein said top section and said bottom section comprise a high thermal conductivity material selected from a group of copper, aluminum, graphite, graphite foams and metal foams of aluminum and copper, wherein the top section further being configured to receive back-scattered electrons generated by the electron beam impact at the respective stationary x ray target and predominantly redirect the back-scattered electrons away from said electron beam source,
wherein said top section comprises a plurality of grooves to trap a plurality of back-scattered electrons and prevent said plurality of back-scattered electrons from hitting said respective stationary x ray target.

54. The system of claim 53, wherein said target substrate comprises a plurality of cooling channels.

55. The system of claim 54, wherein said cooling channels are configured to allow a coolant to be passed through said cooling channels to dissipate heat generated at said respective stationary x ray target and wherein said coolant comprises a liquid.

56. The system of claim 54, wherein said cooling channels comprise heat storage materials to dissipate heat generated at said respective stationary x ray target.

57. The system of claim 53, wherein said top section comprises a notch to trap a plurality of back-scattered electrons and to prevent said plurality of back-scattered electrons from hitting said respective stationary x ray target.

58. The system of claim 53, wherein said top section comprises a plurality of cooling channels.

59. The system of claim 58, wherein said cooling channels are configured to allow a coolant to be passed through said cooling channels and wherein said coolant comprises a liquid.

60. The system of claim 58, wherein said cooling channels comprise heat storage materials.

61. The system of claim 60, wherein said heat storage materials comprise phase change materials.

* * * * *